United States Patent [19]
Wyss

[11] Patent Number: 6,116,236
[45] Date of Patent: Sep. 12, 2000

[54] RESPIRATOR

[76] Inventor: Gerard J. Wyss, 25133 Woodburn Rd., Woodburn, Ind. 46797

[21] Appl. No.: 08/968,487

[22] Filed: Nov. 12, 1997

[51] Int. Cl.[7] .................................................. A61M 15/00
[52] U.S. Cl. ............................... 128/200.24; 128/206.11; 128/206.19
[58] Field of Search ..................... 128/200.24, 205.27, 128/206.24, 206.25, 206.19, 206.11; 606/199, 204.45

[56] References Cited

U.S. PATENT DOCUMENTS

| | | | |
|---|---|---|---|
| 2,323,199 | 6/1943 | Bulbulian | 128/206.24 |
| 4,201,205 | 5/1980 | Barthdomen | 128/205.25 |
| 4,231,363 | 11/1980 | Grimes | 128/205.25 |
| 4,266,540 | 5/1981 | Panzik et al. | 128/207.13 |
| 4,354,488 | 10/1982 | Bartos | 128/205.25 |
| 4,657,010 | 4/1987 | Wright | 128/205.25 |
| 4,951,664 | 8/1990 | Niemeyer | 128/206.24 |
| 5,431,158 | 7/1995 | Tirotta | 128/206.21 |
| 5,476,091 | 12/1995 | Johnson | 128/200.24 |
| 5,533,499 | 7/1996 | Johnson | 128/200.24 |
| 5,533,503 | 7/1996 | Doubek et al. | 128/200.24 |
| 5,546,929 | 8/1996 | Muchin | 128/200.24 |
| 5,549,103 | 8/1996 | Johnson | 128/200.24 |
| 5,553,605 | 9/1996 | Muchin | 128/200.24 |
| 5,558,089 | 9/1996 | Castiglione | 128/206.24 |
| 5,609,150 | 3/1997 | Maged | 128/201.18 |
| 5,611,333 | 3/1997 | Johnson | 128/200.24 |
| 5,611,334 | 3/1997 | Muchin | 128/200.24 |
| 5,617,849 | 4/1997 | Springett | 128/206.24 |
| 5,640,974 | 6/1997 | Miller | 606/204.45 |
| 5,653,224 | 8/1997 | Johnson | 128/200.24 |
| 5,803,075 | 9/1998 | Yavitz | 128/206.24 |
| 5,842,470 | 12/1998 | Ruben | 128/206.19 |

*Primary Examiner*—Aaron J. Lewis
*Attorney, Agent, or Firm*—Lundy and Associates

[57] ABSTRACT

A new and improved respirator comprising a respirator body configured to fit over at least the nose of a person wearing the respirator. The respirator body has an interior and an exterior surface. The interior surface has a portion which fits over the nose of the person wearing the respirator. A nasal dilator is secured to the interior surface portion of the respirator body. The nasal dilator has an adhesive substance thereon which overlays a person's nose when the respirator body is worn to provide a seal between the respirator and the person's nose and cheeks and to promote breathing of the person wearing the respirator.

30 Claims, 5 Drawing Sheets

RESPIRATOR

BACKGROUND OF THE INVENTION

The present invention pertains to a respirator and more particularly to a new and improved respirator which ensures a snug fit over a person's nose and the cheeks on the sides of the nose without impairment of one's breathing and possibly improving the nasal breathing of the person wearing the respirator. The present invention also pertains to a new and improved method of fitting a respirator to a person's face.

Respirators, also referred to as "filtering face masks" have long been provided to wear over the breathing passages of a person's face for three common purposes: (1) to prevent impurities or contaminants from entering the wearer's breathing passage; (2) to provide a warm air layer within the respirator to allow the person wearing the respirator to breathe warmer than ambient air, and in cold weather to exhale warm air into a warmer than ambient environment so as to prevent condensation and freezing on the person wearing the respirator, and (3) to protect others from being exposed to pathogens or other contaminates exhaled by the wearer. In the first situation, a respirator is worn in an environment where air contains particles harmful to the wearer, for example, in an auto body shop, in a foundry, or when spray painting or sanding drywall joints in places of limited ventilation. In the second situation, a respirator is worn in an environment where there is a high risk of infection, for example, in an operating room, or in a crowded working environment. Respirators are now required to be worn by persons in certain environments.

Two types of respirators are available for such use. The first type fits over the nose and leaves the mouth uncovered by the respirator. A second type covers both the nose and the mouth. In both types, common deficiencies have been found in the respirator due to the material from which the respirator is made and the work environment of the wearer. Therefore, it is highly desirable to provide a new and improved respirator.

Prior art respirators are generally deficient in the manner in which they provide a seal around the nose and to the cheeks of a person wearing the respirator. Most of these prior art respirators do not seal well to the face, and thus, when one breathes into the respirator, breath leaks around the periphery between the respirator and the face. Thus, it is highly desirable to provide a new and improved respirator for providing a snug fit over a person's nose and to the cheeks on both sides of the nose.

Persons wearing glasses also experience on cooler days excessive fogging of the glasses, requiring persons to remove the glasses and clean the glasses periodically. Some respirators provide such a poor seal between the nose and the respirator that moist air from exhaling not only leaks between the respirator and the nose, but is directed onto the glasses causing them to fog repetitively so quickly after wiping them, that the person has few other alternatives other than to remove the glasses, or remove the respirator. Thus, it is highly desirable to provide a new and improved respirator which provides an improved seal between the respirator and the face of the person wearing the respirator. It is also highly desirable to provide a new and improved respirator which provides an improved seal between the respirator and the face of the person wearing the respirator such that even upon heavy breathing, a person's glasses will not fog.

Many respirators now are required to be worn by persons doing rigorous physical activity. Asthmatics who are exercising wear such respirators, and workmen doing hard physical labor wear such respirators, even when the weather is very warm. Thus, it is more important than ever that the seal around the face remain adequate during use when the wearer is undergoing rigorous breathing, such as during heavy physical exercise, and is perspiring profusely. It is therefore highly desirable to provide a new and improved respirator having an improved seal around the periphery of the respirator to the face when the person wearing the respirator is doing rigorous physical exercise and gasping for air and exhaling strongly.

Nose clips are commonly used on respirators to achieve a snug fit over the nose of the wearer. Conventional nose clips are in the form of pliable, soft linear strips of aluminum, see for example U.S. Pat. Nos. 5,307,776 or 4,600,002, or 3,603,315. See also U.K. Patent Application GB 2103471. Conventional nose clips help to provide a snug fit over the nose of the wearer, but the fit frequently has been obtained at the expense of restricted flow through the wearer's nasal passages. In addition, conventional nose clips are known to exert a clamping pressure on the wearer's nose and the cheekbones and this clamping pressure can also cause discomfort to the wearer. Other nose clips have the drawback of not extending over the bridge of the nose and therefore are not very good candidates for commercial use on conventional cup shaped or full face or partial face respirators. See for example U.S. Pat. Nos. 2,153,437 and 2,568,254. Such nose clips are not preferred for respirators used during rigorous physical exercise in which the person gasps for breath and exhales strongly. It is therefore highly desirable to provide a new and improved respirator which has an improved seal between the face of the person wearing the respirator not at the expense of restricting airflow through the wearer's nasal passages.

A portion of the human population have some malformation of the nasal passage which makes breathing difficult even when not undergoing rigorous exercise. Thus, it is highly desirable to provide a new and improved respirator which can be utilized by those people who have difficulty breathing because of malformations in their nasal passages. It is further highly desirable to provide a new and improved respirator which enhances the breathing of most people. It is also highly desirable to provide a new and improved respirator which can be worn during rigorous exercise and by athletes. Finally, it is highly desirable to provide a new and improved respirator which enhances breathing of all persons wearing the respirator by dilating the nasal passages.

Respirators such as the one disclosed herein are most desirable if they are disposable after use. Therefore, it highly desirable to provide a new and improved respirator which is of simple construction, convenient to use and can be manufactured relatively inexpensively so as to be disposable.

Finally, it is highly desirable to provide a new and improved respirator having all of the above-identified features.

SUMMARY OF THE INVENTION

It is therefore an object of the invention to provide a new and improved respirator.

It is also an object of the invention to provide a new and improved respirator which has an improved seal between the face of the person wearing the respirator not at the expense of restricting flow through the wearer's nasal passages.

It is also an object of the invention to provide a new and improved respirator which provides an improved seal between the respirator and the nose of the face of the person wearing the respirator.

It is also an object of the invention to provide a new and improved respirator which provides an improved seal between the respirator and the nose of the face of the person wearing the respirator such that even upon heavy breathing, a person's glasses will not fog.

It is also an object of the invention to provide a new and improved respirator having an improved seal around the periphery of the respirator to the face even when the person wearing the respirator is doing rigorous physical exercise and gasping for air and exhaling strongly.

It is also an object of the invention to provide a new and improved respirator which has an improved seal between the face of the person wearing the respirator not at the expense of restricting flow through the wearer's nasal passages.

It is also an object of the invention to provide a new and improved respirator which can be utilized by those people who have difficulty in breathing because of malformations in their nasal passages.

It is also an object of the invention to provide a new and improved respirator which enhances the breathing of most people.

It is also an object of the invention to provide a new and improved respirator which can be worn during rigorous exercise and by athletes.

It is also an object of the invention to provide a new and improved respirator which enhances breathing of all persons wearing the respirator by dilating the nasal passages.

It is also an object of the invention to provide a new and improved respirator which has simple construction, is convenient to use and can be manufactured relatively inexpensively so as to be disposable It is finally an object of the invention to provide a new and improved respirator having all of the above-identified features.

In the broader aspects of the invention there is provided a new and improved respirator comprising a respirator body configured to fit over at least the nose of a person wearing the respirator. The respirator body has an interior and an exterior surface. The interior surface has a portion which fits over the nose of the person wearing the respirator. A nasal dilator is secured to the interior surface portion of the respirator body. The nasal dilator has an adhesive substance thereon which overlays a person's nose when the respirator body is worn to provide a seal between the respirator and the person's nose and cheeks and to promote breathing of the person wearing the respirator.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
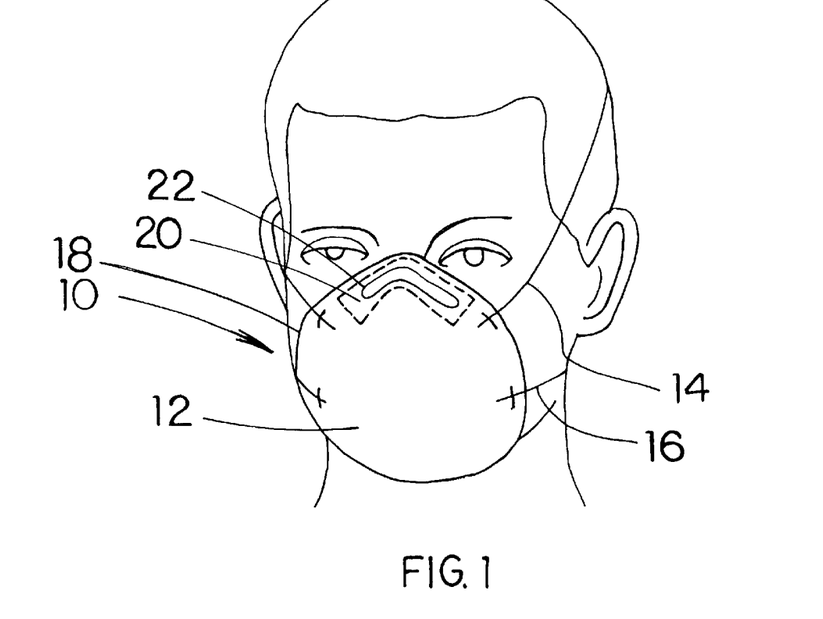
FIG. 1 is a prospective view showing the new and improved respirator of the invention having dual headstraps and being worn over the nose and mouth of a person.
Figure 2:
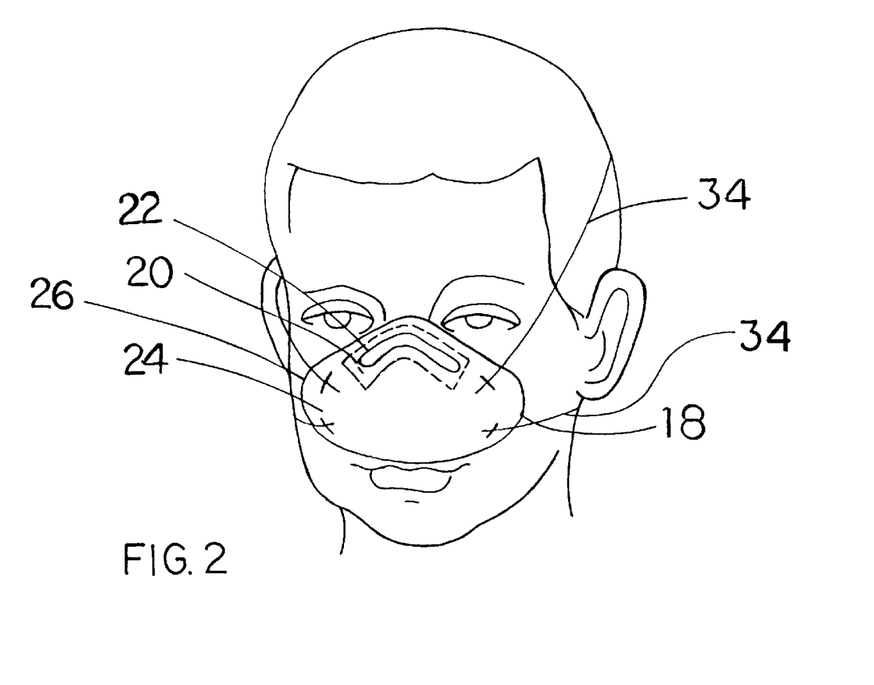
FIG. 2 is a figure like FIG. 1 of the new and improved respirator of the invention having only a single headstrap and being worn only over the nose of a person.
Figure 3:
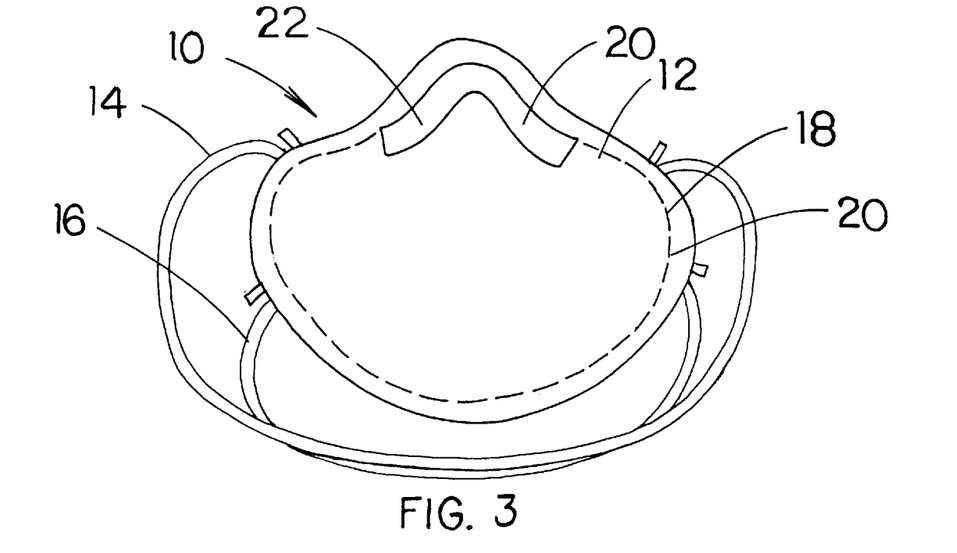
FIG. 3 is a rear view of the new and improved respirator of the invention as shown in FIG. 1.

FIGS. 1–4 illustrate the new and improved respirator of the invention. FIGS. 1 and 3 show a full nose and mouth respirator 10. Respirator 10 comprises a respirator body 12 which extends from just beneath the eyes of the person wearing the respirator 10 to below the mouth and covers both the nasal and the oral breathing passages of the person wearing the respirator 10. The body 12 is secured to the face of the person wearing the respirator 10 by two straps 14, 16. Strap 14 is secured adjacent the top of the respirator body 12. Strap 16 is secured adjacent the bottom of the respirator body 12. Respirator body 12 has a periphery 18 which extends around the edge of the respirator body 12. In a specific embodiment, periphery 18 may be provided with an adhesive 20 for sealing the respirator 10 to the face. In other specific embodiments, the seal is provided at the periphery 18 of the respirator 10 without adhesive when the straps 14, 16 are snugly placed around the head of the person wearing the respirator 10. In those embodiments in which adhesive 20 is used for sealing the respirator 10 to the face, the respirator may be provided with a skin cleanser such that the adhesive 20 will provide a seal between the respirator 10 and the face which will hold throughout all of the activity of the person wearing the respirator 10.

Respirator 10 generally conforms to the wearer's face around the whole periphery 18. There sometimes is a radical change in the contour of a person's face around the nose and air leaks may occur in this area. To prevent leakage, respirator body 12 is provided with a nose dilator 22. Dilator 22 is positioned adjacent the top of the periphery 18 to overlay the nose and nasal passages of the wearer as will be described hereinafter more fully.

Figure 4:
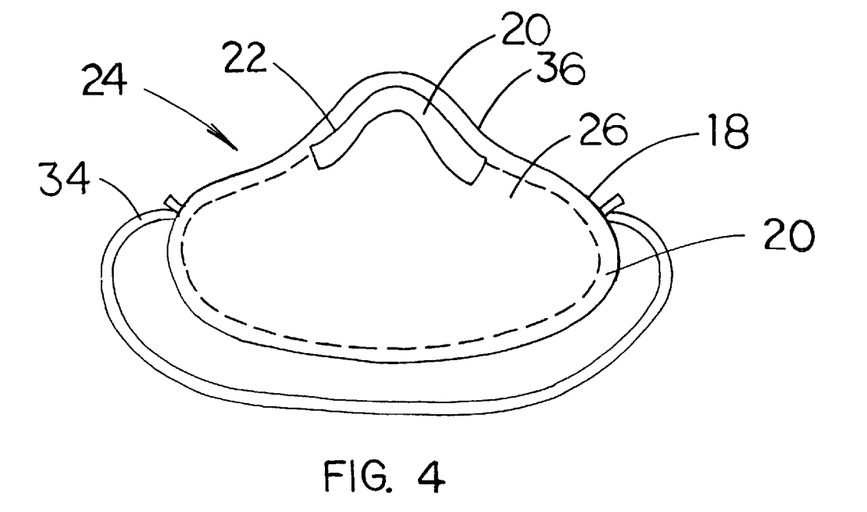
FIG. 4 is a rear view like FIG. 3 of the new and improved respirator of the invention shown in FIG. 2.

Referring now to FIGS. 2 and 4, a new and improved respirator 24 of the invention is shown with respirator body 26 which extends from below the eyes of the wearer to below the nose of the wearer. The mouth of the wearer is not covered by the respirator body 26, such that the wearer of the respirator can freely speak without hindrance by respirator 24. Respirator body 26 is provided with straps 34 and has a perimeter 18 on which adhesive 20 may be positioned to provide a seal between the respirator 24 and the face of the wearer as above described. A seal between the nose and the cheeks on the opposite side of the nose is provided by a dilator 22 secured to the inside of the respirator adjacent the top portion of the periphery 18 similar to the respirator 10 shown in FIGS. 1 and 3.

In a specific embodiment, dilator 22 may be secured to the body 12 and 26 by a suitable adhesive. In a specific embodiment the adhesive 20 at periphery 18 and the adhesive securing dilator 22 to the body 12, 26 both can be any porous, acrylic, pressure sensitive, bio-compatible adhesive. An industrial grade bi-axially oriented polyester such as MYLAR type A can also be used. In a specific embodiment adhesive 20 may be an acrylic, pressure sensitive, biocompatible transfer tape such as that designated 3M 1509 offered by and available from Minnesota, Mining & Manufacturing Inc. or an acrylic, pressure sensitive, biocompatible transfer adhesive material such as that designated 1368 B offered by and available from the Betham Corporation.

Figure 6:
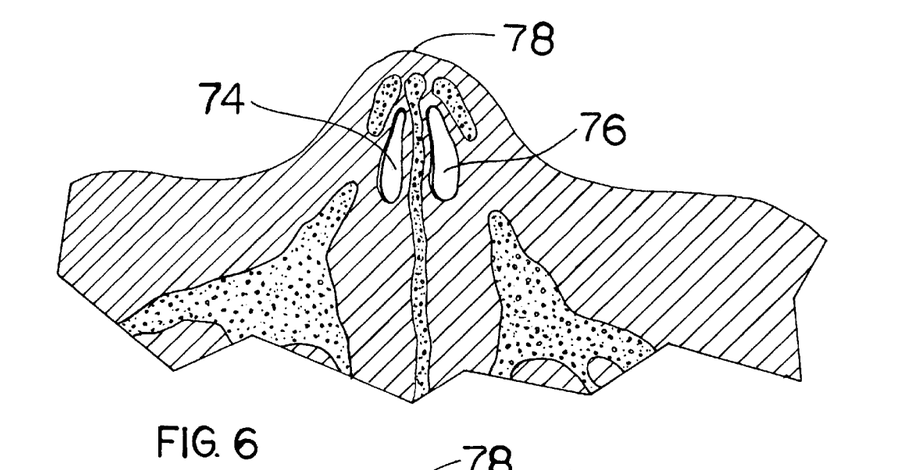
FIG. 6 is a cross sectional view of the nose and the nasal passages showing the nose in a state wherein appreciable flow of air is occurring in the nasal passages.
Figures 7, 8:
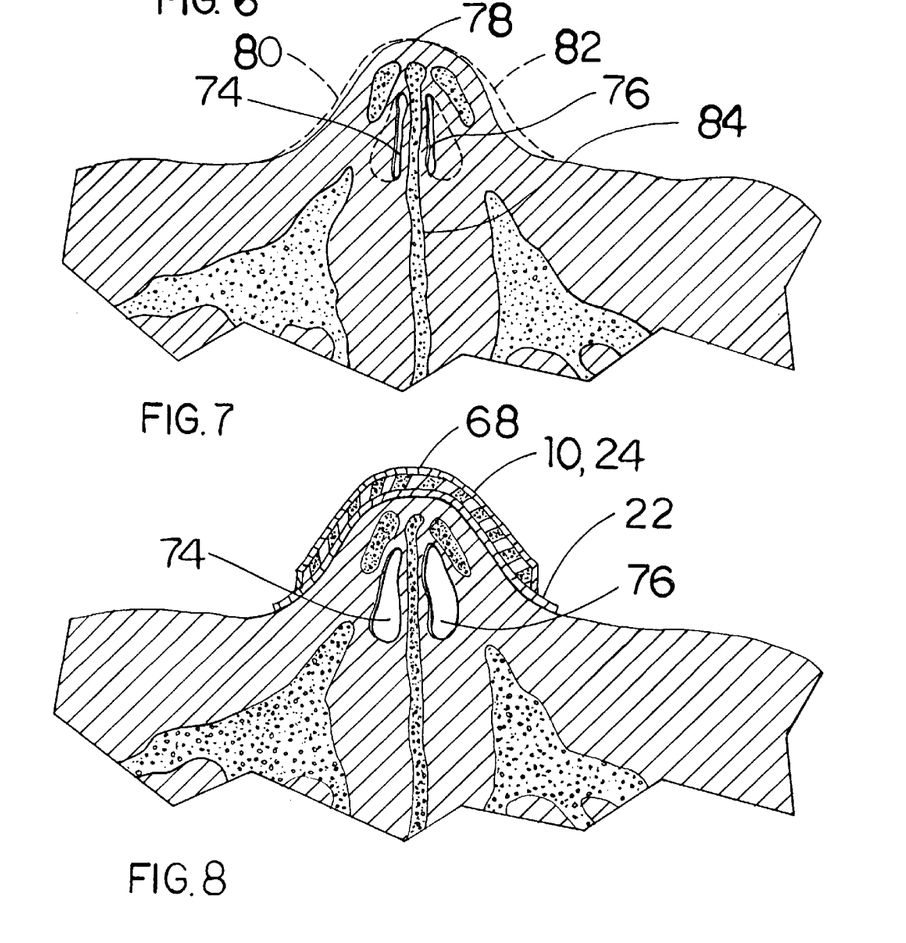
FIG. 7 is a cross sectional view similar to FIG. 6 showing the state of the nose during inhalation.
FIG. 8 is a cross sectional view similar to FIG. 6 showing the state of the nose during inhalation with the new and improved respirator of the invention.

FIG. 6 is a sectional view showing the nose in a state where appreciable flow of air is occurring in the nasal passages. FIG. 7 is a sectional view similar to FIG. 6 showing the state of the nose during inhalation. FIG. 8 is a sectional view similar to FIG. 6 showing the state of the nose during inhalation with the nasal dilator 22 secured to the new and improved respirator 10, 26 of the invention in place.

Figure 5:
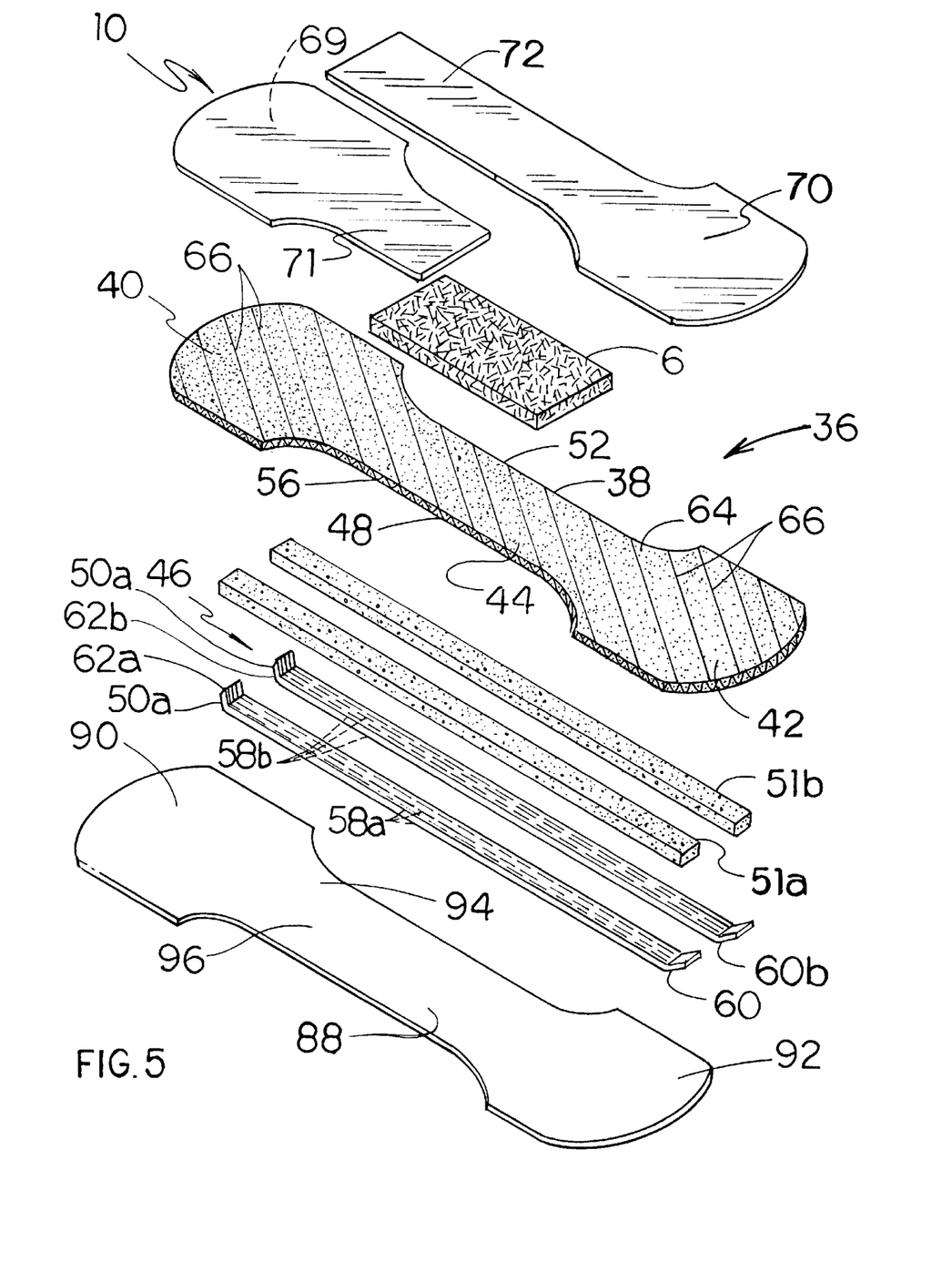
FIG. 5 is an exploded view of the nasal dilator of the new and improved respirator of the invention used to provide a seal between the respirator and the nose and cheeks of the person wearing the respirator.

The nasal dilator 22 is illustrated in FIG. 5 in exploded fashion. The nasal dilator 22 comprises a truss member 36 including a flexible strip of material 38 having a first end region 40 and a second end region 42 coupled to the first end region 40 by way of an intermediate segment 44. The width of the intermediate segment 44 is less than the width of the first and second end regions 40 and 42. The flexible strip of material 38 is preferably formed of an interwoven piece of fabric that allows the skin of the nose to breathe with maximum comfort and minimal irritation. As an alternative, the strip of material 38 may be formed of a plastic film.

In a specific embodiment, flexible strip 38 may be a suitable nonwoven spunlaced 100% polyester fabric which is offered by and available from E. I. DuPont Nemours & Co. under the trade name SONTARA fabric typically having a breaking strength property in a ratio approximately 2:1 as determined by the machine direction or warp, relative to the cross direction or fill of the fabric. In addition, SONTARA fabric typically has an elongation percentage ratio of approximately 3:1 as determined by the resulting elongation of the four equal forces in the cross and machine direction of the fabric. Machine direction of the fabric is parallel to the longitudinal extent of the strip of material 38.

The truss member further includes resilient means 46 secured to a first side 48 of the strip of material 38. The resilient means 46 includes a first resilient band 50a secured by a first adhesive member 51a to the first side 48 of the strip of material 38. The first resilient band 50a is secured to the strip of material 38 adjacent a first edge 52 of the intermediate segment 44. In addition, a second resilient band 50b, spaced from the first resilient band 50a, is secured by a second adhesive member 51b to the first side 48 of the strip of material 38. The second resilient band 50b is secured to the strip of material 38 adjacent a second edge 56 of the intermediate segment 44. The first and second resilient bands 50a and 50b are oriented generally parallel to one another and substantially parallel to the longitudinal extent of the flexible strip of material 38. In a specific embodiment, resilient bands 50a and 50b are formed of a polymer material such as an industrial grade, bi-axially oriented polyester, such as MYLAR type A offered by E. I. DuPont Nemours & Co. which is cut to approximately 0.080 inches to 0.135 inches in widths from 0.010 inch thick stock. Using a polymer material which is relatively thin such as just described for each of the first and second resilient bands 50a and 50b enhances the axially, torsional flexibility of each of these bands about the longitudinal extent of each depending upon the width of the bands actually used.

In a specific embodiment, first and second adhesive members 51a and 51b may be of a material such as above-described with regard with adhesive 20. In other specific embodiments, each of the first and second adhesive members 51a and 51b may be formed of an adhesive material such as double sided adhesive, foam tape.

Each of the first and second resilient bands 50a and 50b may include a plurality of grooves 58a and 58b, respectively, that extend substantially parallel to the respective resilient band 50a and 50b. As seen best in FIG. 5, the grooves 58a and 58b are formed in the exposed sides of the first and second resilient bands 50a and 50b, (i.e., the sides of the first and second resilient bands 50a and 50b opposite that to which the first and second adhesive members 51a and 51b are secured). The grooves 58a and 58b create areas of reduced material to enhance the flexibility of the first and second resilient bands 50a and 50b in a direction perpendicular to the plurality of grooves 58a and 58b. In addition, each of the first and second resilient bands 50a and 50b may include first angled ends 60a and 60b, respectively, and second angled ends 62a and 62b, which extend towards the first side 48 of the strip of material 38 and helps to prevent the first and second resilient bands 50a and 50b from separating from the strip of material 38 and the first and second adhesive members 51a and 51b when the truss member 36 is flexed.

Figures 9, 10:
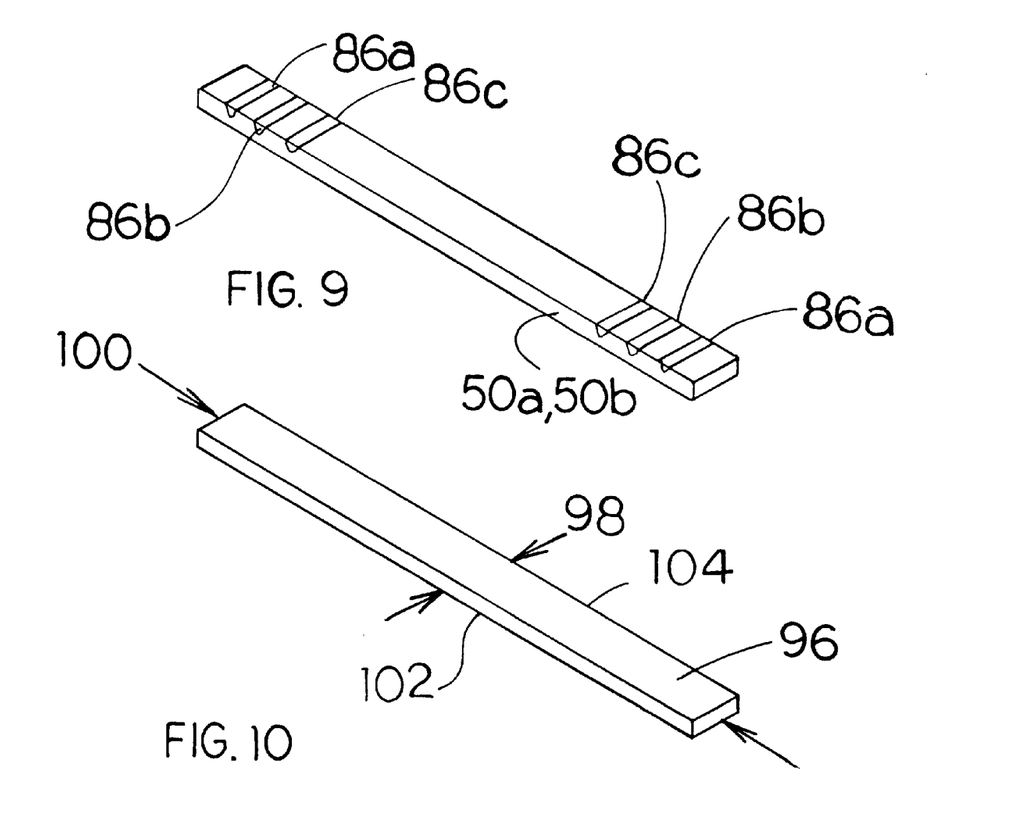
FIG. 9 is a prospective view of an alternative resilient band.
FIG. 10 is prospective view of a spring which is used alternatively in place of the resilient bands of FIGS. 5 and 9.

Alternatively, to the grooves 58a and 58b or in addition to the grooves 58a and 58b, as shown in FIG. 9, a sequence of three notches, 86a, 86b, and 86c may be provided in each of the first and second resilient bands 50a and 50b. Notches 86a are nearest the extreme ends of each of the first and second resilient bands 50a and 50b, and are the deepest notches and, for example, in a resilient band with a 2.60 inch length and a 0.135 inch width, this notch would be typically about 0.15 inches inward from the resilient band end nearest thereto with a depth of about 80% to 98% of the thickness of the resilient band, typically about 90% to 95% of the thickness. The next notches inward to this example, notches 86b, would be located about 0.10 to 0.20 inches closer to the middle with a depth of about 60% to 90% of the resilient band thickness, typically about 68% to 72%. Finally, the last notch shown in each sequence and closest to the middle of the resilient band, notch designated as 86c, would typically be another 0.10 to 0.20 inches closer to the middle, but with a depth of only about 40% to 70% of the resilient band thickness, typically about 38% to 42%.

Further notches could be included in sequence extending closer to the middle of corresponding resilient bands, and different depths for each of the notches could be used. The effect of introducing these notches ever less deep in the sequence thereof toward the middle is to monotonically decrease, or taper off, the effective spring constant along the two half-lengths of each of the resilient bands starting from the middle thereof. The deepest notches reduce the effective spring constant the most so that locating them at the ends of the bands is quite effective in reducing the peel forces at the ends of the resilient bands resulting from the spring force and the motion of the skin therebeneath. The other notches of lesser depth as one proceeds to go the center of the band reduces the spring constant less at each location thus giving an increasing effective spring constant along the directions from the ends of the of the resilient bands toward the center. As a result, the desired pull on the outer wall tissues of the user's nose can be set by the type of material, length, thickness and width to provide the desired pull on those tissues while being reduced sufficiently, as will be described, to avoid undue peel forces occurring between the pressure sensitive adhesive beneath the ends of each these bands and the skin to which it is attached.

As seen in FIG. 5, a second side 64 of the strip of material 38 includes a layer of an adhesive substance 66 that extends over the first and second end regions 40 and 42 and the intermediate segment 44. The adhesive substance 66 is bio-compatible with the skin of the nose. A padded element 68 is secured to the median of the intermediate segment 44 via the adhesive substance 66. Readily removable, first and second release liners 69 and 70, respectively, cover the adhesive substance 66 on the first and second end regions 40 and 42, respectively, of the strip of material 38. The first and second release liners 69 and 70 cover the adhesive substance 66 and remain in place on the strip of material 38 until the nasal dilator 42 is to be used. The first and second release liners 69 and 70 also include extensions 71 and 72, respectively, that cover the padded element 68 and further act to protect the padded element 68 until the nasal dilator 22 is to be secured to the nose of a wearer.

In a specific embodiment, element 68 may be porous sponge material or any other liquid absorbent material.

Truss 36 may also include a flexible strip of top material 88 having a first end region 90 and a second end region 92 and an intermediate segment 94 with the same size and shape in plan view as base material strip 38 has in plan view. A bottom surface 96 of top material strip 88 includes a layer of an adhesive substance 20 that extends over the first and second end regions 90 and 92 and over the intermediate segment 94. Top material strip 88 covers first and second resilient bands 50a and 50b and first side 48 of base material strip 38 and is secured thereto by adhesive substance layer 20.

Top material strip 88 aids in preventing first and second resilient bands 50a and 50b from separating from base material strip 38 and interface adhesive material strips 51a and 51b in those situations where truss 36 is flexed by movement of the skin thereunder on which it is being used. In addition, top material strip 88 limits to some degree base material strip 38 by together providing a stiffer material in the major plane thereof to provide a geometrically more stable combination which permits installing and removing dilator 22 more easily. Top material strip 88 is preferably a porous, nonwoven material with adhesive substance 20 provided thereon such as that designated 3M 1533 offered by, and available from Minnesota, Mining & Manufacturing, Inc. In another specific embodiment, a fabric suitable for forming base material 38 can be obtained with adhesive substance provided thereon such as the material 3M 1776 offered by, and available from Minnesota, Mining & Manufacturing, Inc.

In the specific embodiment shown in FIG. 10, resilient bands 50a and 50b and top material 88 can be replaced by a single spring member 96 which would occupy 25% to about 55% of the surface area of strip material 38. Spring member 96 would be centrally located in the surface 48 of the strip 38. Spring member 96 also would define a width 98 which would be about ½ to ¾ of the width of the narrowest portion of the strip 38. Spring member 96 is centrally located along the length of the strip 38. The length of the spring member 96 is between about ½ to ¾ of the length of the flexible strip 38.

In the specific embodiment, when the spring member 96 is located over the bridge of the nose, the opposite flat surfaces 102, 104 of the spring member 96 extend over the bridge of the nose and at least partly beyond the bridge and both sides of the bridge.

In use on the nose there are only the spring member 96 and flexible strip of material 38. There is an adhesive bond between the flexible strip 38 and the spring member 96 and selectively, in one form of the invention there is also adhesive on the surfaces 102, 104 of the spring member 96. When the flexible strip 38 is located on the nose of a wearer, the end portions 40, 42 extend outwardly to separate the skin covering the nasal passages of the wearer by the spring member 96. The flexible strip 38 is lifted in part from the nasal passages in the vicinity of the end portions 40, 42. In position on the nose, flat surface 104 of the spring member 96 engages directly on the nose through an adhesive strip.

Attached to the nose, spring member 96 and flexible strip 38 have a natural position contrary to the curvature formed by the location of the spring member 96 over the bridge of the nose and adjacent the nasal passages. Spring member 96 and flexible strip 38 preferably have a position with a curvature contrary to the shape of the curvature formed from one nasal passage over the bridge of the nose to the second nasal passage. The contrary curvature acts to place an increased amount of spring action on the dilator 22 such that dilation action on the nasal passages is enhanced when in use. The increased spring action is caused by the counter stress put into the spring member 96 prior to usage by the position of contrary curvature.

In a specific embodiment, flexible strip 38 is stretched prior to adhering it to the spring member 96. The stretch action between spring member 96 and the flexible strip 38 acts to place the spring 96 into a contrary curvature. This curvature is counter curvature relative to the curvature when in use.

In still another specific embodiment the first and second adhesive members 51a and 51b include a carrier of a transparent 3 mil polyethylene film, with an adhesive which is hypoallergenic, pressure sensitive acrylate adhesive thereon. The adhesive system may be No. 1509, Double Coated Medical Tape on Liner from 3M Company, 3M Center, St. Paul, Minn. This product is a double-coated transparent polyethylene film, coated on both sides with a hypoallergenic, pressure-sensitive, acrylate adhesive, supplied on a paper liner. The double coated tape is wound with the liner on the outside of the roll. The liner is bleached Kraft-Glassine paper, silicone coated on both sides.

As seen in FIG. 8, the nose includes a first nasal passage 74, a second nasal passage 76 and a portion of the nose known as the bridge 78 located between the first and second nasal passages 74 and 76. FIG. 4 shows the state of the first and second nasal passages 74 and 76 when no appreciable flow of air is occurring through the nasal passes 74 and 76. Due to a malformation, such as a deviated septum or swelling due to allergic reactions, outer wall tissues 80 and 82 of the first and second nasal passages 74 and 76, respectively, tend to be drawn in, (i.e., collapse) during inhalation, (see FIG. 7). This drawing in during inhalation is caused by reduced air pressure within the first and second nasal passages 74 and 76 as a result of an increase in air velocity as the in drawn breath travels through the first and second nasal passages 74 and 76. The portion, (i.e., the position) of the outer wall tissues 80 and 82 drawn in during inhalation is that which is located between the nasal cartilage 84 and the entrance to the nasal passages 74 and 76. This drawing in of the outer wall tissues 80 and 82 causes nasal blockage. The nasal dilator 22 secured to the respirator 10 of the present invention remedies this problem.

To secure the nasal dilator 22 to the nose, the first and second release liners 69 and 70 are removed from the flexible strip of material 38 to expose the adhesive substance 66. As seen in FIGS. 1 and 6, the nasal dilator is placed on the exterior of the nose such that the intermediate segment 44 traverses the bridge 78 of the nose and the first and second end regions 40 and 42 contact the outer wall tissues 80 and 82 of the first and second nasal passages 74 and 76. The adhesive substance 66 on the first and second end regions 40 and 42 releasably secure the truss member to the outer wall tissues 80 and 82 of the first and second nasal passages 74 and 76. As seen in FIG. 8, the padded element 68 creates an absorbent adhesive void between the truss member and the bridge 78. This absorbent adhesive void absorbs moisture due to perspiration or the like. With the nasal dilator 22 in place about the nose, the resiliency of the first and second resilient bands 50a and 50b, (i.e., the tendency of the resilient bands to return to their normally planar state shown in FIG. 5) acts to stabilize the outer wall tissues 80 and 82 and thereby prevents the outer wall tissues 80 and 82 of the first and second nasal passages 74 and 76 from drawing in during breathing, (i.e., during inhalation). In addition, the flexibility of the strip of material 38 and the first and second adhesive members 51a and 51b, flexibility of the first and second bands 50a and 50b due to the grooves 58a and 58b, all allow the nasal dilator 22 to closely conform to the curves of the nose of each individual wearer.

This nasal dilator 22 is of efficient design and effectively prevents the outer wall tissues 80 and 82 of the first and second nasal passages 74 and 76 of the nose from drawing in during breathing. In addition, the nasal dilator 22 provides effective relief of nasal blockage during inhalation without the irritation and discomfort normally associated with nasal dilators that are inserted within the nasal passages.

The new and improved respirator 10, 24 of the invention provides an improved seal between the respirator and the face of the person wearing the respirator. The seal is so good that even during cool weather, the seal between the new and improved respirator 10, 24 of the invention and the face of the person wearing the respirator, even upon heavy breathing, a person's glasses will not fog. The new and improved respirator 10, 24 provides such a good seal even when a person wearing the respirator is doing rigorous physical exercise and gasping for air and exhaling strongly. The new and improved respirator 10, 24 provides the wearer with normal or improved breathing while wearing the respirator. Normal or improved breathing and improved seal between the respirator and the face of the person is provided by the new and improved respirator 10, 24 of the invention not at the expense of restricting airflow to the wearer's nasal passages. The new and improved respirator 10, 24 can enhance the breathing of most people and can be worn while performing rigorous exercise and by athletes. The new and improved respirator 10, 24 provides all of these features, and yet is simple in construction, convenient to use, and can be manufactured relatively inexpensively so as to be disposable.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A respirator comprising a respirator body configured to fit over and cover the nose of a wearer, said respirator body when worn leaving uncovered the eyes and the mouth of said wearer, said respirator body having an interior and exterior surface and a peripheral surface surrounding said interior surface, a nasal dilator secured to the interior surface of said respirator body, said nasal dilator having a surface facing away from said respirator and forming a part of said interior surface of said respirator, said nasal dilator surface having an adhesive substance thereon thereby to secure said respirator and dilator to said wearer's nose and the cheeks on the opposite sides thereof to promote breathing, said peripheral surface having an adhesive substance thereon to secure said respirator to the face of said wearer between the eyes and the mouth and to prevent the leaking of exhaled air between the respirator and the face.

2. The respirator of claim 1 wherein said nasal dilator comprises a unitary truss member, said truss member having a first end member adapted to engage the outer wall tissue of a first nasal passage, said truss member having a second end member adapted to engage the outer wall tissue of a second nasal passage, said truss member having an intermediate member configured to transverse a portion of the nose located between the first and second nasal passages, said truss member being resilient and having the tendency when flexed to return to its normally planar state and to stabilize the first and second outer wall tissues of the nose thereby preventing the outer wall tissue of the first and second nasal passages from drawing in during breathing, said truss member being capable, at least in part, of deformation that allows the truss member to conform to the outer wall tissue of the nasal passages of the nose without exceeding its elastic limit.

3. The respirator of claim 2 wherein said truss member includes a flexible strip of material defining said first and second end member and said intermediate member, said member being secured to a first side of said flexible strip of material by way of a deformable means, said resilient member defining the normally planar state of the truss member.

4. The respirator of claim 3 further comprising an adhesive substance located on a second side of said flexible strip of material at the first and second end regions thereof for releasably securing the truss member to the outer wall tissue of the nasal passages.

5. The respirator of claim 4 further including first and second release liners covering the adhesive substance on said first and second end regions, respectively, of said flexible strip of material, said first and second release liners being readily removable from the flexible strip of material to expose the adhesive substance and permit said truss member to be secured to the outer wall tissue of said first and second nasal passages in fitting said respirator body over a wearer's nose.

6. The respirator of claim 4 wherein said resilient member includes at least one resilient band orientated substantially parallel to a longitudinal axis of said flexible strip of material, the resiliency of at least said resilient band acting to prevent the outer wall tissue of the first and second nasal passages from drawing in during breathing.

7. The respirator of claim 2 wherein said intermediate segment of said truss member includes an adhesive void, said truss member being configured to extend over a nose such that said intermediate segment transverses an exterior region of the bridge of the nose with the adhesive void located between the truss member and the bridge, said first end region engaging an exterior surface of the outer wall tissue of said first nasal passage and said second end region engaging the exterior surface of the other wall tissue of a second nasal passage.

8. The respirator of claim 2 wherein said truss member has a pair of spaced apart end surfaces terminated by end edges at opposite ends of said truss member and having means for generating restoring forces including at least a first resilient band of selected thickness in said truss member extending between said end edges such that, if said spaced apart end surfaces are forced toward one another from initial positions to thereby substantially reduce direct spacing therebetween by a spacing reduction force external to said truss member, restoring forces result in said truss member which tend to restore said direct spacing between said end surfaces with such restoring forces being due to at least said first resilient band, and further having means for reducing said restoring forces at selected portions of said first resilient band comprising a plurality of notches formed at selected locations along said truss member and extending inwardly from at least one side thereof, said notches reducing that thickness of said first resilient band occurring at each said selected locations to less than those thicknesses occurring immediately on either side of each said notch; and an engagement means adhered to said end surfaces adapted for engaging exposed surfaces of said outer wall tissues, and for remaining so engaged against said restoring forces.

9. The respirator claim 8 wherein said first resilient band is of essentially a selected thickness substantially everywhere except at locations of said notches in said plurality thereof, said notches exceeding in depth a third of that thickness and being oriented substantially perpendicular to said extent of said truss member.

10. The respirator of claim 8 wherein each of said plurality of notches extends across corresponding widths of said first resilient band at said locations.

11. The respirator of claim 2 wherein said truss member is formed of a material that allows the skin of a nose to breathe to maximize comfort and minimize irritation.

12. The respirator of claim 1 wherein said nasal dilator stabilizes said outer wall tissue by dilating the first and second nasal passages thereby to prevent the outer wall tissue of the first and second nasal passages from drawing in during breathing.

13. The respirator of claim 1 wherein said dilator comprises a truss member having a normally, substantially planar state, said truss member including a first end region adapted to engage the outer wall tissue of a first nasal passage; a second end region adapted to engage the outer wall tissue of a second nasal passage; an intermediate segment configured to traverse a portion of a nose located between the first and second nasal passages; a flexible strip of material defining the first and second end regions and the intermediate segment; a first resilient band secured to a first side of the flexible strip of material adjacent a first edge thereof; a second resilient band secured to the first side of the flexible strip of material at a second edge thereof, the second resilient band being spaced from and extending generally parallel to the first resilient band; and a deformable means for allowing the truss member to conform to the outer wall tissue of the nasal passages of a nose through the deformable means capability of being deformable, said deformable means being positioned in at least portions of the first and second end regions and the intermediate segment to secure said first and second resilient bands to said first side of said flexible strip, said first and second resilient bands defining a normally planar state of said truss member such that the inherent tendency of the truss member to return to this normally planar state when flexed acts to stabilize the outer wall tissue and thereby prevent the outer wall tissue of the first and second nasal passages from drawing in during breathing.

14. The respirator of claim 1 wherein said dilator comprises a truss member having a normally planar state, including a first end region adapted to engage the outer wall tissue of a first nasal passage; a second end region adapted to engage the outer wall tissue of a second nasal passage; an intermediate segment, the truss member being unitary from the first end region to the second end region with the intermediate segment being configured to traverse an exterior region of a bridge of a nose located between the first and second nasal passages, the inherent tendency of the truss member to return to its normally planar state when flexed acting to stabilize the outer wall tissue and thereby prevent the outer wall tissue of the first and second nasal passages from collapsing when inhaling; and a deformable means secured in at least a portion of the first and second end regions and the intermediate segment for enhancing the flexibility of the truss member in a direction substantially perpendicular to a longitudinal extent of the truss member.

15. The respirator of claim 1 wherein said dilator comprises a truss member having a normally, substantially planar state, said truss member including a first end region engaging with an adhesive substance thereon an exterior outer surface of the outer wall tissue of a first nasal passage; a second end region engaging with an adhesive substance thereon an exterior surface of the outer wall tissue of a second nasal passage; an intermediate segment configured to traverse a portion of a nose located between said first and second nasal passages by extending about an exterior region of the bridge of that nose with there being an adhesive void located between the truss member and that exterior region of the bridge of a user's nose as provided by an absorbent element, the inherent tendency of the truss member to return to its normally planar state when flexed acting to stabilize the outer wall tissue and thereby prevent the outer wall tissue of the first and second nasal passages from drawing in during breathing; and a deformable means for allowing the truss member to conform to the outer wall tissue of the nasal passages of a nose through the deformable means capability of being deformable, the deformable means defining at least a portion of the first and second end regions and the intermediate segment.

16. The respirator of claim 15 wherein said truss member having a pair of spaced apart end surfaces which, if forced toward one another from initial positions to substantially reduce direct spacing therebetween by a spacing reduction force external to said truss, results in restoring forces in said truss tending to restore said direct spacing between said end surfaces; and engagement means adhered to said end surfaces and capable of engaging exposed surfaces of nasal outer wall tissues sufficiently to remain so engaged against said restoring forces.

17. The respirator of claim 1 wherein said nasal dilator comprises a truss member comprising a first end region adapted to engage the outer wall tissue of a first nasal passage; a second end region adapted to engage the outer wall tissue of a second nasal passage; an intermediate segment coupling the first end region to the second end region and configured to traverse a portion of a nose located between the first and second nasal passages; and a resilient member extending along said truss member and having end portions that terminate at least at sections of said end edges of said first and second end regions, said resilient member acting to stabilize said outer wall tissues so engaged thereby to prevent such outer wall tissues of the first and second nasal passages from drawing in during breathing.

18. The respirator of claim 1 wherein said nasal dilator comprises a truss member comprising a first end region adapted to engage the outer wall tissues of a first nasal passage; a second end region adapted to engage the outer wall tissue of a second nasal passage; an intermediate segment coupling the first end region to the second end region and configured to traverse a portion of a nose located between the first and second nasal passages; a flexible strip of base material extending over at least a portion of the first and second end regions and the intermediate segment; and resilient means extending along the truss member including a first resilient band secured to the flexible strip of base material adjacent a first edge thereof and a second resilient band secured to the flexible strip of base material adjacent a second edge thereof such that each have end portions that terminate at least at sections of said end edges of said first and second end regions with the second resilient band being spaced from and extending generally parallel to the first resilient band, said resilient means acting to stabilize the outer wall tissue and thereby prevent the outer wall tissue of the first and second nasal passages from drawing in during breathing.

19. The respirator of claim 1 wherein said nasal dilator comprises a truss member comprising a first end region adapted to engage the outer wall tissue of a first nasal passage; a second end region adapted to engage the outer wall tissue of a second nasal passage; an intermediate segment coupling the first end region to the second end region and configured to traverse a portion of a nose located between the first and second nasal passages; and resilient means extending along the truss member and having end portions that terminate at least at sections of end edges of the first and second end regions, a back cut provided extending into said truss member at each of said end edges of the first and second end regions which is located between a portion of the resilient means and a further portion of the truss member at first and second end regions of the truss member for preventing inadvertent delamination of the strip of base material from the outer wall tissue of the first and second nasal passages.

20. The respirator of claim 1 wherein said nasal dilator comprises a truss member comprising a pair of spaced apart end regions each having a side terminated by end edges at opposite ends of said truss such that if said spaced apart end region sides are forced toward one another from initial positions to substantially reduce said spacing therebetween by a spacing reduction force external to said truss, restoring forces result in said truss sufficient to restore a substantial fraction of said spacing between said end region sides absent such spacing reduction forces; and an engagement means adhered to said end region sides and capable of engaging exposed surfaces of such outer wall tissues sufficiently to remain so engaged against said restoring forces, said pair of end region sides with said engagement means adhered thereto each including as part thereof at least one corresponding extension with said extension being separated in part from at least some other portion of that said end region of which it is a part with said separation extending into that said end region from said end edge thereof.

21. The respirator of claim 1 wherein said nasal dilator comprises a truss member comprising an elongated spring member for bridging a human nose, the spring member having an outer edge and opposite flat surfaces and being for extending over a bridge of the nose and being for engaging the user's nose; a flexible pad having a surface area and peripheral edge, said pad being for engaging the spring member and extending around the spring member so that there is a surface perimeter area of the pad formed between the outer edge of the spring member and the peripheral edge of the pad, said spring being inset from the peripheral edge of the pad substantially around the pad, and wherein the surface perimeter area includes an adhesive for adhering to skin of the nose; and an adhesive means between said spring member and said pad such that the spring member on one of its flat surfaces adheres with said pad, the arrangement being such that when said spring member is located over the bridge of the nose, the opposite flat surface of the spring member extends over the bridge of the nose and at least partly beyond the bridge on both sides of the bridge, and the surface perimeter area of said pad adheres to skin of the nose, the arrangement being such that, in use, said spring is located between the nose and the pad.

22. The respirator of claim 1 wherein said nasal dilator comprises a truss member comprising an elongated spring member for bridging a human nose, said spring member having an outer edge and opposite flat surfaces and being for extending over a bridge of the nose; a flexible pad having a surface area and peripheral edge, said pad being for engaging said spring member and extending around said spring member so that there is a surface perimeter area of said pad formed between the outer edge of said spring member and said peripheral edge of said pad, said spring being inset from the peripheral edge of said pad substantially around said pad and wherein said surface perimeter area includes an adhesive means for adhering to skin of the nose; an adhesive between said spring member and said pad such that said spring member on one of its flat surfaces adheres with said pad, the arrangement being such that when said spring member is located over the bridge of the nose, said opposite flat surface of said spring member extends over the bridge of the nose and at least partly beyond the bridge on both sides of the bridge, and said surface perimeter area of said pad adheres to skin of the nose and wherein, in use on the nose, there are said spring member, said adhesive pad, the adhesive between said pad and said spring member, and means for adhering said spring member directly to the user's nose including an adhesive on said spring member.

23. The respirator of claim 1 wherein said nasal dilator comprises a truss member comprising an elongated spring member for bridging a human nose, said spring member having an outer edge and opposite flat surfaces and being for extending over a bridge of the nose; a flexible pad having a surface area and peripheral edge, the pad being for engaging said spring member and extending around said spring member so that there is a surface perimeter area of the pad formed between the outer edge of said spring member and the peripheral edge of said pad, the spring being inset from the peripheral edge of said pad substantially around the pad, and wherein the surface perimeter area includes an adhesive for adhering to skin of the nose, an adhesive between said spring member and said pad such that said spring member on one of its flat surfaces adheres with the pad, the arrangement being such that when said spring member is located over the bridge of the nose, the opposite flat surface of the spring member extends over the bridge of the nose and at least partly beyond the bridge on both sides of the bridge, and the surface perimeter area of said pad adheres to skin of the nose; and wherein, when in position on the nose, a flat surface of the spring member engages directly on the nose.

24. The respirator of claim 1 wherein said nasal dilator comprises a truss member comprising an elongated spring member for bridging a human nose, said spring member having an outer edge and opposite flat surfaces and being for extending over a bridge of the nose; a flexible pad having a surface area, said pad being for engaging said spring member and extending beyond said spring member so that there is a surface area of said pad formed between the outer edge of said spring member and said peripheral edge of said pad, and wherein said surface area includes an adhesive for adhering to skin of the nose; an adhesive between said spring member and said pad such that said spring member on one of its flat surfaces adheres with said pad, the arrangement being such that when said spring member is located over the bridge of the nose, said spring member extends over the bridge of the nose and at least partly beyond the bridge on both sides of the bridge, and said surface area of said pad adheres to skin of the nose; and wherein said spring member is formed of a resilient, synthetic resinous material, and said spring member and pad, when unattached to the nose, has a natural position contrary to a curvature formed by location of said spring member over the bridge of the nose and adjacent to the nasal passages, and wherein the position of contrary curvature is obtained by relatively stretching said pad longitudinally prior to affixation with the spring member.

25. The respirator of claim 1 wherein said nasal dilator comprises a truss member comprising an elongated spring member for bridging a human nose, said spring member having an outer edge and opposite flat surfaces and being for extending over a bridge of the nose and wherein said spring member is a resilient member; a flexible pad having a surface area and peripheral edge, said pad being for engaging the spring member and extending around the spring member so that there is a surface perimeter area of said pad formed between said outer edge of said spring member and said peripheral edge of said pad whereby said spring is inset from said peripheral edge of said pad substantially around said pad, and wherein said surface perimeter area includes an adhesive for adhering to skin of the nose; and an adhesive between said spring member and said pad such that said spring member on one of its entire engaging surfaces wholly adheres with said pad, said spring member having being die cut and been located as an island within the surface area of said pad, the arrangement being such that when said spring member is located over the bridge of the nose, said opposite flat surfaces of the spring member extend over the bridge of the nose and at least partly beyond the bridge on both sides of the bridge, and said surface perimeter area of said pad adheres to skin of the nose, and wherein in use on the nose there are only said spring member with adhesive for adhering to the nose, said adhesive pad, and the adhesive between said pad and said spring member with said spring member being positioned between the nose and the pad.

26. The respirator of claim 1 wherein said nasal dilator comprises a truss member comprising an elongated spring member for bridging a human nose, said spring member having an outer edge and opposite flat surfaces and being for extending over a bridge of the nose; a flexible ad having a surface area and peripheral edge, said pad being for engaging the spring member and extending around the spring member so that there is a surface perimeter area of said pad formed between said outer edge of said spring member and said peripheral edge of the pad whereby said spring is inset from said peripheral edge of said pad substantially around said pad, and wherein said surface perimeter area includes an adhesive for adhering to skin of the nose; said spring member and said pad, respectively, including ends, said ends of said spring member being located inwardly from said ends of said pad member such that when said pad member is located on the nose of a wearer, said ends of said spring are urged outwardly and separate from nostrils of the wearer, such that said pad is lifted in part from the nostrils in the vicinity of said ends of said spring member, and said resilient member and pad have a position, when non-adhering to the nose, with a curvature contrary to the shape of the curvature formed from one nasal passage with said spring member being positioned between the nose and said pad.

27. The respirator of claim 1 wherein said nasal dilator comprises a truss member comprising an elongated spring member for bridging a human nose, said spring member having an outer edge and opposite flat surfaces and being for extending over a bridge of the nose and wherein said spring member is a resilient member; a flexible pad having a surface area and peripheral edge, said pad being for engaging said spring member and extending around the spring member so that there is a surface perimeter area of said pad formed between the outer edge of said spring member and said peripheral edge of said pad, said spring being inset from said peripheral edge of said pad substantially around said pad and wherein said surface perimeter area includes an adhesive for adhering to skin of the nose; an adhesive between said spring member and said pad such that said spring member on one of its flat surfaces adheres with said pad, said spring member having been die cut and located as an island within said surface area of said pad, the arrangement being such that when said spring member is located over the bridge of the nose, the opposite flat surface of said spring member extends over the bridge of the nose and at least partly beyond the bridge on both sides of the bridge, and said surface perimeter area of said pad adheres to the skin of nose, and wherein in use on the nose there are only said spring member with adhesive for adhering to the nose, the adhesive pad, and the adhesive between said pad and said spring member; and wherein, when in position on the nose, a flat surface of said spring member with adhesive engages directly to the user's nose.

28. The respirator of claim 1 wherein said nasal dilator comprises a truss member comprising an elongated spring member for bridging a human nose and for engaging a user's nose; a flexible pad having a surface area, said pad being for engaging said spring member and extending beyond said spring member so that there is a surface area of said pad formed between the outer edge of said spring member and said peripheral edge of said pad, and wherein said surface area includes an adhesive for adhering to skin of the nose; and an adhesive means between said spring member and said pad such that the spring member adheres with said pad, the arrangement being such that when said spring member is located over the bridge of the nose, said spring member extends over the bridge of the nose and at least partly beyond the bridge on both sides of the bridge, and said surface area of said pad adheres to the skin of the nose, the arrangement being such that, in use, said spring is located between the nose and the pad.

29. The respirator of claim 1 wherein said nasal dilator comprises a truss member comprising an elongated spring member for bridging a human nose; a flexible pad having a surface area, the pad being for engaging said spring member and extending beyond said spring member so that there is a surface area of the pad formed between the outer edge of said spring member and said peripheral edge of the pad, and wherein said surface area includes an adhesive for adhering to skin of the nose; an adhesive between said spring member and said pad such that said spring member adheres with said pad, the arrangement being such that when said spring member is located over the bridge of the nose, said spring member extends over the bridge of the nose and at least partly beyond the bridge on both sides of the bridge, and said surface area of said pad adheres to the skin of the nose; and wherein, when in position on the nose, said spring member engages directly on the nose.

30. The respirator of claim 1 wherein said adhesive substance on said nasal dilator surface and said adhesive substance on said peripheral surface are different adhesives.

* * * * *